United States Patent [19]

Sanders et al.

[11] 4,292,308

[45] Sep. 29, 1981

[54] TREATMENT OF ANIMALS EXPOSED TO OR SUBJECT TO EXPOSURE TO ORGANOPHOSPHATE ANIMAL POISONOUS NERVE AGENTS

[75] Inventors: Murray J. Sanders, Delray Beach, Fla.; James A. Vick, Annandale, Va.

[73] Assignee: Biotherapeutics, Inc., Delray Beach, Fla.

[21] Appl. No.: 68,446

[22] Filed: Aug. 21, 1979

[51] Int. Cl.³ .................. A61K 35/58; A61K 39/38
[52] U.S. Cl. ............................... 424/98; 424/2; 424/12
[58] Field of Search .............. 424/2, 9, 12, 85, 88, 424/89, 95, 98

[56] References Cited

U.S. PATENT DOCUMENTS 3,888,977  6/1975  Sanders ..................... 424/12
4,162,303  7/1979  Sanders ..................... 424/9

OTHER PUBLICATIONS

Lee, Snake Venoms, Springer Verlag, N.Y., 1979, pp. 552, 568, 574–576.
Tu, Venoms; Chemistry & Mol. Biol., John Wiley, N.Y., 1977, pp. 178–184.

Primary Examiner—Anna P. Fagelson
Attorney, Agent, or Firm—Murray and Whisenhunt

[57] ABSTRACT

A method is provided for treatment of animals exposed to or subject to exposure to organophosphate animal poisonous nerve agents. The animals are injected with an effective amount of modified neurotoxin, preferably intramuscularly or intravenously, either prior to or shortly after exposure to the nerve agents. Particularly when the injection is administered prior to exposure, and where the dosage is of a higher amount, certain compositions achieve 100% survivors of Rhesus monkeys, even in the face of a challenge of 5 $LD_{50}$ of the nerve agent.

15 Claims, No Drawings

TREATMENT OF ANIMALS EXPOSED TO OR SUBJECT TO EXPOSURE TO ORGANOPHOSPHATE ANIMAL POISONOUS NERVE AGENTS

The invention relates to a method of treatment of animals, particularly humans, which are exposed to, or which are subject to exposure to, organophosphate animal poisonous nerve agents. More particularly, the invention concerns said treatment with a composition of matter known as modified neurotoxin.

BACKGROUND OF THE INVENTION

As is well known, a family of compounds, known collectively as "organophosphates" are poisonous to animals by virtue of attacking the nervous system of animals. A number of these compounds are used in conventional insecticides and others, which are highly toxic, such as Soman, Tabun and Sarin, have potential as military nerve agents. Yet other of these compounds are industrial chemicals.

Low dosages in animals of the organophosphate animal poisonous nerve agents may be successfully treated by conventional therapies, especially the less toxic members of the family of compounds, but higher dosages, especially of the more toxic members of the family of compounds, most often prove fatal to animals. In these latter cases, the usual therapy for these nerve agents is that of atropine, which is administered after exposure to the nerve agent. Atropine has some mitigating effects, but is mainly useful in preventing death only where the amount of nerve agent received does not substantially exceed the lethal dose thereof. When a substantial excess of a lethal dose is received, atropine is essentially ineffective in preventing death. Additionally, atropine has dangerous side-effects, and indiscriminate use thereof, e.g., in anticipation of a nerve agent exposure, could produce very serious results, including death, even if the nerve agent exposure does not occur.

Accordingly, it would be of substantial benefit to provide a method for treatment of animals, especially humans, exposed to, or subject to exposure to, organophosphate animal poisonous nerve agents, i.e., both a prophylaxis and a therapy for nerve agent exposure.

OBJECTS OF THE INVENTION

It is therefore an object of the invention to provide a method for treatment of mammals exposed to, or subject to exposure to, organophosphate animal poisonous nerve agents. It is a further object of the invention to provide such method which is a prophylaxis, i.e., is administered prior to exposure. It is a further object of the invention to provide such a method which is a therapy, i.e., is administered subsequent to exposure. It is a further object of the invention to provide such method wherein there are essentially no adverse side effects of the treatment. Other objects will be apparent from the following description and claims.

BRIEF DESCRIPTION OF THE INVENTION

The invention is based, primarily, on the unexpected discovery that a known composition of matter, referred to as modified neurotoxin, is effective as both a prophylactic and therapeutic agent in the treatment for organophosphate animal poisonous nerve agents. Thus, when the modified neurotoxin is administered as a prophylactic agent, in sufficient dosages, test results show that is can not only be effective in preventing deaths in animals, even when challenged with massive doses of the nerve agent, but essentially avoids any serious effects of the challenge.

Thus, briefly stated, the present invention provides a method for the treatment of animals exposed to, or subject to exposure to, organophosphate animal poisonous nerve agents, comprising administering to the animal an effective amount of modified neurotoxin.

DETAILED DESCRIPTION OF THE INVENTION

Organophosphate animal poisonous nerve agents are known compositions of matter and are basically organophosphate compounds which are cholinesterase inhibitors. Organophosphates characteristically produce their toxic effects by inhibiting cholinesterase and producing respiratory/cardiovascular paralysis. The mechanisms of these lethal agents are not completely understood, but it appears that the receptors of both the peripheral and central nervous systems are affected. These nerve agents can be transmitted into the body simply by contact with the skin or by inhalation. The most lethal of the organophosphates animal poisonous nerve agents are Soman, Tabun, and Sarin.

Modified neurotoxin is a known composition of matter and has been widely disclosed in literature. It has therapeutic properties for treatment of progressive degenerative neurological diseases of the motor nerve cell origin to the neuromuscular junction, axions, and nerve myelin sheaths, and has been extensively used in the treatment of amyotrophic lateral sclerosis. It may be defined as detoxified and neurotropically active modified snake venom neurotoxin wherein the composition exhibits at least a 30% inhibition of plaques in the Semliki Forest Virus test and a bioassay shows that the composition is atoxic.

Modified neurotoxin is prepared from neurotoxic snake venoms which are detoxified in known manners, e.g., by oxygenation at a pH of above 7 and a temperature of 15° to 40° C. until atoxicity is reached, whereafter the detoxification procedure is ceased and the composition remains neurotropic.

The neurotoxic snake venom, from which modified neurotoxin is prepared, is preferably of the Naja genus and/or Bungarus genus, although other venoms, such as *Crotalus terrificus* may be used. Modified neurotoxin will demonstrate at least a 30% inhibition of plaques in the Semliki Forest Virus test, which demonstrates its neurotropic character.

Modified neurotoxin has been extensively disclosed in the art, but concise summaries thereof are contained in U.S. Pat. No. 3,888,977 and U.S. Pat. No. 4,126,667, the entire disclosures of which are incorporated herein by reference and relied upon for disclosure. Those patents also describe in detail the Semliki Forest Virus test and an improvement thereof is disclosed in U.S. patent application Ser. No. 807,654. In view of the extensive disclosures in the art of modified neurotoxin, for sake of conciseness, the details of that known composition of matter will not be repeated herein.

However, very briefly stated, neurotoxic snake venoms are detoxified by known procedures, a modification of the known Boquet technique (Ann. Inst. Pasteur 66:379–396, 1941), being the preferred procedure. The venom is dissolved in a solvent, especially water, and usually at concentrations of 3% or less, with an optional antifoam added, e.g., a food-grade silicone compound.

Oxygen or an oxygen producing material is placed in the solution, e.g., CP hydrogen peroxide (30% solution) along with an activator therefor, e.g., copper sulphate. The pH is adjusted to above 7, preferably less than 10, with a suitable base, such as sodium hydroxide. Buffers, such as alkali metal phosphate or acetate buffers may be used. The solution is maintained at temperatures between 15° and 40° C., more preferably 20° C. to 40° C. and the oxygenation reaction is allowed to continue for up to about 30 days, especially between 8 hours and 16 days. Thereafter, the detoxification reaction is stopped by adding a deactivator for the $H_2O_2$, e.g., CP catalase. Optionally the modified neurotoxin composition is dialyzed against a semi-permeable, e.g., cellulose acetate, in a phosphate buffer-sodium chloride solution, to cause transfer of undesired ions. The composition is then sterilized in a sterile filter, e.g., about 0.22 microns, and 1/10,000 Merthiolate is added thereto. Final pH adjustment to about 6.8 is made with a food-grade acid and the product is assayed for potency by the Semliki Forest Virus test and tested for sterility and atoxicity.

In this latter regard, a tissue culture, such as chick embryo fibroblastic tissue culture of cells on glass or baby hamster kidney cells is overlaid with a gelled nutrient such as Hank's solution with lactalbumin. The Semliki Forest Virus is inoculated on the sheet of cells and the number of resulting plaques show the titer of the virus. To determine the potency of the modified neurotoxin, the same test is run, but the cells are washed with the modified neurotoxin prior to inoculation of the Semliki Forest Virus. The number of Plaque Forming Units reduction between the test with the Semliki Forest Virus and the test with the modified neurotoxin is determined and expressed as either a percent reduction or log reduction. The potency of the modified neurotoxin will always show at least a 30% inhibition of plaques, especially at least a 50% inhibition and almost always at least a 70 to 75% inhibition. Generally speaking, the modified neurotoxin is considered of high potency when the plaque reduction is one log or more.

The potency of the modified neurotoxin will vary somewhat, depending upon the source of the neurotoxic snake venom. Thus, it is preferred to use a species of a Naja genus or a species of the Bungarus genus, and preferably combinations thereof. The ratios in such combinations can vary widely, but it is preferred that the ratio of Naja venom to Bungarus venom be between 400:1 to 1:1, and especially between 80:1 and 10:1, on a weight basis. As has been reported in the literature, and the above-identified patents, the venom of such snakes contains a multitude of chemical compounds, including various enzymes, beyond the toxins which are the compounds from which the active ingredients of the modified neurotoxin is formed. If desired, the toxins can be separated by known techniques, e.g., gel chromatography, and only the toxins can be used in producing the modified neurotoxin. For purposes of the present specification and claims, the term "modified neurotoxin" is defined to include that composition made from either the whole venom or the toxic portions thereof.

The composition is preferably administered by injection, e.g., either subcutaneously, intraperitoneally, intramuscularly or intravenously, but it is preferred that the injection be either intramuscularly or intravenously, since this mode of administration allows the modified neurotoxin to reach and protect the nerve cells in a more rapid manner. As can be appreciated, in view of the deadly nature of the organophosphate animal poisonous nerve agents, the present composition has not been tested on humans. It has been tested on monkeys and mice and the required dosage for humans has been projected from the required dosage for animals. As will be seen from the data which follows, certain formulations of the modified neurotoxin can produce 100% survivors in Rhesus monkeys at 10 cc dosages, even with challenges of 5 $LD_{50}$ of organophosphate animal poisonous nerve agent. Also, 50% survivors are achieved at 4 cc dosages. Projecting this data on the basis of a human with a 68 kilogram body weight, protection is calculated to be provided by a 1 cc dosage, when the amount of organophosphate animal poisonous nerve agent received by the human is 1 $LD_{50}$ or less. However, preferred dosages would be at least 4 or 5 cc, e.g., 10 cc or more. Those dosages are based on a modified neurotoxin composition solution having therein 1% by weight of the detoxified venom. The dosages, of course, will be adjusted for greater or lesser percentages of detoxified venom, and for the case where only the toxic portions, rather than the whole venom, are used in producing the modified neurotoxin, as explained above. Usually, however, the modified neurotoxin is in a diluted form and will contain no more than 10% of the active modified neurotoxin, either in the form of that derived from whole venom or that derived from the toxic portions thereof.

The injection of the modified neurotoxin is preferably administered prior to exposure to the nerve agent. This provides time for the modified neurotoxin to reach the neurons and protect those neurons from the lethal effects of the nerve agent. The modified neurotoxin will persist in the body for three days or more, but preferably the injection is no more than 24 hours prior to exposure of the nerve agent and more preferably no more than ½ hour prior to the exposure of the nerve agent.

The modified neurotoxin is also effective in preventing or at least mitigating the effects of exposure to the nerve agent even when administered subsequent to exposure to the nerve agents. However, since the nerve agents are quite lethal and may act very rapidly, it is preferred that the injection is no more than 1-6 hours subsequent to, e.g., 20 minutes subsequent to, exposure to the nerve agent and more preferably the injection is no more than 10 minutes subsequent to exposure to the nerve agent.

While not necessary, if desired, the treatment with the modified neurotoxin, either prior to or after exposure to the nerve agent, may be accompanied by conventional therapies, e.g., the known therapy of using atropine (1 to 6 mg. per 68 kilogram body weight, I.M.). Of course, the atropine would not be used unless actual exposure to the nerve agents occurs. Other conventional therapies may be used with the modified neurotoxin, e.g., oxime (50-110 mg. I.M.).

An important advantage of the modified neurotoxin therapy is that it is atoxic and has no known significant side effects. Extensive use of modified neurotoxin in the treatment of human patients suffering from amyotrophic lateral sclerosis has not shown side effects other than an occasional reddening of the injection site and other minor skin discomforts. A chronic toxicity study of modified neurotoxin showed that animals receiving large dosages of modified neurotoxin over a two year period had no physiological side effects. Thus, the modified neurotoxin may be repeatedly used on humans subject to exposure to nerve agents, without incurring any risk by virtue of administration of the modified neurotoxin.

The invention will be illustrated by the following examples, but it is to be understood that the invention is not limited thereto and extends to the breadth of the foregoing disclosure and following claims. In the examples, as well as in the specification and claims, all percentages and parts are by weight unless otherwise indicated.

EXAMPLE 1

Modified neurotoxin was prepared according to the method of Example 2 of U.S. Pat. No. 3,888,977. Thus, 40 grams of desiccated *Naja naja* venom and 0.5 grams of desiccated *Bungarus multicinctus* venom are added to 3,600 ml of phosphate buffered aqueous solution at a pH of 7.5. A trace amount of silicone antifoam (Dow-Corning) is added and the mixture is stirred to dissolve the venom. 2 ml of 1% CP solution of copper sulfate is added with stirring. 80 ml of 30% hydrogen peroxide is added to the solution. This solution is placed in a volumetric flask and the phosphate buffered aqueous solution is added to make 4,000 ml (a nominal 1% solution). The solution is incubated at 37° C., and the pH is monitored. The pH is maintained at about 7.5 by the addition of one normal sodium hydroxide solution as required. Aliquots of the solution are tested daily for toxicity by inoculating 0.5 ml of undiluted solution intraperitoneally per mouse in 20 gram mice. At the end of 14 days of detoxification 20 mice showed no deaths in 24 hours at this level of inoculation. Also, the detoxification is tested by giving a dose of 5 ml to 350 gm guinea pigs and no deaths occurred in 24 hours. The bulk solution is then mixed with 3 mg of catalase per ml of solution. Finally, the solution is filtered through clarifying membranes and a final 0.22 micron filter and 1/10,000 concentration of merthiolate is established and the pH is adjusted to 6.8 with 1 N hydrochloric acid. The Semliki Forest Virus test showed 3.8 log reduction of P.F.U. The so produced modified neurotoxin was tested for sterility and bioassayed for safety and lack of toxicity.

Ten Rhesus monkeys were housed in standard cages and conditioned for at least 30 days to insure stabilization of the monkeys after transportation thereof. Each monkey was fully examined, including blood chemistry, in order to confirm that the monkeys were free of diseases or defects. The monkeys were restrained by a squeeze cage and injected in the lateral thigh muscle with the modified neurotoxin at the dosage levels indicated in the Table below (monkeys 1-10). 30 minutes after injection with the modified neurotoxin, the monkeys were challenged by injection in the contra thigh muscle with a dose based on body weight to provide a 5 $LD_{50}$ of Soman. Each monkey was continuously observed. Death of a monkey was determined by cessation of breathing. Symptoms prior to death were observed, especially the usual convulsions accompanying nerve agent death.

As a control, ten Rhesus monkeys were treated in the same manner but were not given the modified neurotoxin treatment. The control results are also shown in the Table (monkeys 11-20).

EXAMPLE 2

The procedure of Example 1 was repeated, except that the challenge of Soman was 1.5 $LD_{50}$, and two different dosage levels, i.e., 5 cc and 10 cc, were used. The results are also shown in the Table (monkeys 21-24).

This experiment was carried out by an independent laboratory.

EXAMPLE 3

The procedure of Example 1 was repeated except that the amount of *Naja naja* venom was 80 grams and no *Bungarus multicinctus* was used (2% nominal solution of *Naja naja*). Two monkeys (5.4 and 4.8 Kgs) were injected with 10 cc of the solution and challenged with 1.5 $LD_{50}$ of Soman, according to the procedure of Example 1. The monkeys died in 12 and 11 hours, respectively.

A third monkey (7.8 Kg) was injected with 1.5 $LD_{50}$ of Soman and thirty minutes later injected with 10 cc of the solution of this example. The monkey died in 5 hours.

As can be seen from the above examples, the control monkeys, challenged with 5 $LD_{50}$ of Soman, die within less than about 0.4 hours. Similar control studies have shown that death occurs within about less than 0.5 hours with 1.5 $LD_{50}$ challenge of Soman. In both cases convulsions normally occur prior to death. When treated with modified neurotoxin, the time to death is substantially extended. The shortest survival time of the test monkeys was 2 hours (monkey #1—1 cc dosage of a 1% solution). With increasing dosages, the time to death is extended and at 4 cc dosage, one monkey survived (monkey #7). At 10 cc dosage with the composition of Example 1, all monkeys survived.

EXAMPLE 4

The procedure of Example 1 was repeated, except that the venom used was only Krait venom (2% solution) and detoxification was completed in about 36 hours. The challenge was with 2.5 $LD_{50}$ of Parathion and 5 cc of the so produced modified neurotoxin was administered. Two monkeys were so challenged and both survived.

By significantly extending the time to death, time is provided to transport a victim to medical facilities where artificial respirators and the like can achieve survivors. At the higher dosages, survivors with no ill effects are achieved, even without medical facilities being available. Thus, the present invention provides a most significant advance in the art and the objects of the invention are achieved.

TABLE OF RESULTS

| Monkey Number | Body Weight, Kg. | Dosage of M.N. cc | Survival Time Hrs. | Symptoms Observed |
|---|---|---|---|---|
| 1 | 5.2 | 1 | 2.0 | no convulsions |
| 2 | 4.8 | 1 | 4.5 | no convulsions |
| 3 | 3.6 | 2 | 9.0 | no convulsions |
| 4 | 4.1 | 2 | 11.0 | no convulsions |
| 5 | 5.2 | 3 | 7.0 | no convulsions |
| 6 | 3.9 | 3 | 13.5 | no convulsions |
| 7 | 4.7 | 4 | survived | no ill effects |
| 8 | 6.1 | 4 | 8.0 | no convulsions |
| 9 | 7.2 | 10 | survived | no ill effects |
| 10 | 7.1 | 10 | survived | no ill effects |
| | | Control | | |
| 11 | 4.8 | — | 0.16 | convulsions |
| 12 | 5.1 | — | 0.13 | convulsions |
| 13 | 3.9 | — | 0.25 | convulsions |
| 14 | 4.4 | — | 0.16 | convulsions |
| 15 | 6.0 | — | 0.08 | convulsions |
| 16 | 3.7 | — | 0.33 | convulsions |
| 17 | 4.9 | — | 0.36 | convulsions |
| 18 | 4.2 | — | 0.18 | convulsions |

TABLE OF RESULTS-continued

| Monkey Number | Body Weight, Kg. | Dosage of M.N. cc | Survival Time Hrs. | Symptoms Observed |
|---|---|---|---|---|
| 19 | 4.5 | — | 0.16 | convulsions |
| 20 | 5.0 | — | 0.30 | convulsions |
| | | 1.5 LD$_{50}$ | | |
| 21 | 5.5 | 5 | 6.0 | no convulsions |
| 22 | 6.1 | 5 | 4.0 | no convulsions |
| 23 | 6.3 | 10 | survived | no convulsions |
| 24 | 7.0 | 10 | survived | no convulsions |

What is claimed is:

1. A method for treatment of an animal exposed to, or subject to exposure to, organophosphate animal poisonous nerve agents, comprising administering to the animal an effective protective amount of detoxified but neurotropically active modified neurotoxin having a Semliki Forest Virus Test Plaque Forming Unit reduction of at least 30%, and being derived from venom selected from the group consisting of venom of a snake of the genus Naja or the genus Bungarus and combinations thereof.

2. The method of claim 1 wherein the administration is by injection either intramuscularly or intravenously.

3. The method of claim 1 wherein the administration is no more than 24 hours prior to exposure to said nerve agents.

4. The method of claim 1 wherein the administration is no more than 20 minutes subsequent to exposure to said nerve agents.

5. The method of claim 3 wherein the administration is no more than 12 hours prior to exposure to said nerve agents.

6. The method of claim 4 wherein the administration is no more than 10 minutes subsequent to exposure to said nerve agents.

7. The method of claim 1 wherein the modified neurotoxin is in a diluted form and contains up to 10% of the active modified neurotoxin.

8. The method of claim 7 wherein the modified neurotoxin has a Semliki Forest Virus Test Plaque Forming Unit reduction of at least 1 log.

9. The method of claim 1 wherein the modified neurotoxin is administered by injecting into the animal and the dosage is at least 1 cc per 68 kilograms of body weight, based on a 1% solution of the modified neurotoxin.

10. The method of claim 1 wherein the said amount is at least 4 cc per kilograms of body weight, based on a 1% solution of the modified neurotoxin.

11. The method of claim 1 wherein the said nerve agent is a cholinesterase inhibitor.

12. The method of claim 11 wherein the nerve agent is selected from the group consisting essentially of Soman, Tabun and Sarin.

13. The method of claim 1 wherein atropine is also administered after exposure to said nerve agents.

14. The method of claim 1 wherein the animal is a human.

15. The method of claim 1 wherein the modified neurotoxin is derived from a combination of venoms from the genus Naja and the genus Bungarus.

* * * * *